(12) United States Patent
Berte' et al.

(10) Patent No.: US 9,487,503 B2
(45) Date of Patent: Nov. 8, 2016

(54) STILBENE OPTICAL BRIGHTENERS

(71) Applicant: 3V SIGMA S.p.A., Milan (IT)

(72) Inventors: Ferruccio Berte', Bergamo (IT); Patrick Alborghetti, Bergamo (IT)

(73) Assignee: 3V SIGMA S.P.A., Milan (IT)

( * ) Notice: Subject to any disclaimer, the term of this patent is extended or adjusted under 35 U.S.C. 154(b) by 61 days.

(21) Appl. No.: 14/333,649

(22) Filed: Jul. 17, 2014

(65) Prior Publication Data
US 2014/0339462 A1 Nov. 20, 2014

(30) Foreign Application Priority Data
Apr. 17, 2014 (IT) ................ MI2014A0726

(51) Int. Cl.
| | | |
|---|---|---|
| C09K 13/06 | (2006.01) |
| C07D 403/12 | (2006.01) |
| C07C 309/15 | (2006.01) |
| C07C 303/22 | (2006.01) |
| C07C 303/32 | (2006.01) |
| D21H 21/30 | (2006.01) |
| D06L 3/12 | (2006.01) |

(52) U.S. Cl.
CPC ........... C07D 403/12 (2013.01); C07C 303/22 (2013.01); C07C 303/32 (2013.01); C07C 309/15 (2013.01); D06L 3/1214 (2013.01); D21H 21/30 (2013.01)

(58) Field of Classification Search
CPC . C07C 303/22; C07C 303/32; C07C 309/15; C07C 403/18; C07D 403/12
USPC ............ 252/79.1, 79.2, 79.3, 79.4; 162/135, 162/162
See application file for complete search history.

(56) References Cited

U.S. PATENT DOCUMENTS

| | | | | |
|---|---|---|---|---|
| 5,025,085 | A * | 6/1991 | Piedrahita ................ | C08K 5/42 525/163 |
| 5,873,913 | A * | 2/1999 | Cowman .............. | C07D 251/68 162/162 |
| 6,210,449 | B1 * | 4/2001 | Rohringer ............ | C07D 251/68 544/193.2 |
| 2005/0022320 | A1 * | 2/2005 | Jackson ................. | C09K 11/06 8/516 |
| 2008/0202716 | A1 * | 8/2008 | Scheffler .............. | C07D 251/68 162/158 |

FOREIGN PATENT DOCUMENTS

| | | |
|---|---|---|
| WO | 9600221 | 1/1996 |
| WO | 0174921 | 10/2011 |
| WO | 20112123425 | 9/2012 |

OTHER PUBLICATIONS

Search Report of priority Italian Application MI20140726 of Jul. 24, 2014.
Written Opinion of priority application IT MI20140726.

\* cited by examiner

*Primary Examiner* — Lan Vinh
(74) *Attorney, Agent, or Firm* — Silvia Salvadori, P.C.; Silvia Salvadori

(57) ABSTRACT

The present invention discloses compounds of 4,4'-diaminostilbene-2,2'-disulphonic acid which are useful as optical brighteners to bleach fibers, cellulose and in particular paper and cardboard.

10 Claims, 3 Drawing Sheets

STILBENE OPTICAL BRIGHTENERS

This Application claims priority to and the benefit of Italian Application No. MI2014A000726 filed on 17 Apr. 2014, the content of which is incorporated herein by reference in its entirety.

The present invention discloses compounds of 4,4'-diaminostilbene-2,2'-disulphonic acid which are useful as optical brighteners to bleach fibres, cellulose and in particular paper and cardboard.

PRIOR ART 4,4'-Diaminostilbene-2,2'-disulphonic acid, generally known as "DAS", is the starting material for many important products used in industry, including many dyes and optical brighteners. Optical brighteners based on DAS chemistry, known as Optical Brightening Agents (OBAs) or Fluorescent Whitening Agents (FWAs), have a number of uses in fields such as detergents, paper, textiles, etc.

One of the most common ways of producing optical brighteners is to replace the amino groups of DAS with variously substituted triazines. This can be done, for example, by reacting DAS under suitable conditions with cyanuryl chloride so that unreacted chlorine atoms remain on the triazine ring. This intermediate reactive species is reacted in turn with other amines or alcohols to obtain the desired products. DAS, cyanuryl chloride and amines or alcohols can obviously be reacted in different sequences, while still producing effective products.

GB 1329565 discloses amines synthesised with the Michael reaction on unsaturated (meth)acrylamide alkanesulphonic monomers. These amines are derived in turn from the reaction of ammonia, primary or secondary alkyl amines, primary or secondary cycloalkylamines, or alkoxyalkyl amines with a (meth)acrylamido alkanesulphonic acid or a salt thereof. Their preparation process and the process for the preparation of a polyurethane dispersion in their presence are also disclosed.

U.S. Pat. No. 4,985,591 discloses a process for the synthesis of a semi-crystalline catalyst for the production of coatings wherein amines obtained with the Michael reaction between a primary monofunctional amine and an alpha,beta-unsaturated amide or ester compound, containing phosphonic or sulphonic groups, are used in the first step.

U.S. Pat. No. 4,090,967 discloses aqueous wetting and film-forming compositions containing fluorinated surfactants, electrolytes, solvents and, among the non-fluorinated surfactants, salts of amino alkylamido alkanesulphonic acids obtained from alkyl amines, cycloalkyl amines, furfuryl amines, morpholine amines and polyvalent amines.

U.S. Pat. No. 5,025,085 discloses compositions of aminoplastic resins wherein the hardening catalysts can also be particular amines derived from the Michael reaction between alkyl amines, alkanolamines, alkoxyalkanolamines and polyamines with a (meth)acrylamido alkanesulphonic acid or a salt thereof.

The stilbene optical brighteners already known, their synthesis processes, their compositions and the corresponding methods and uses in detergents and for bleaching fibres and cellulose and, in particular, paper, have already been extensively described; see, for example, GB 1293804, U.S. Pat. No. 3,532,692, U.S. Pat. No. 4,468,341, U.S. Pat. No. 6,210,449, WO96/00221, EP 860437 and EP 1378545.

DESCRIPTION OF THE INVENTION

Figure 1:
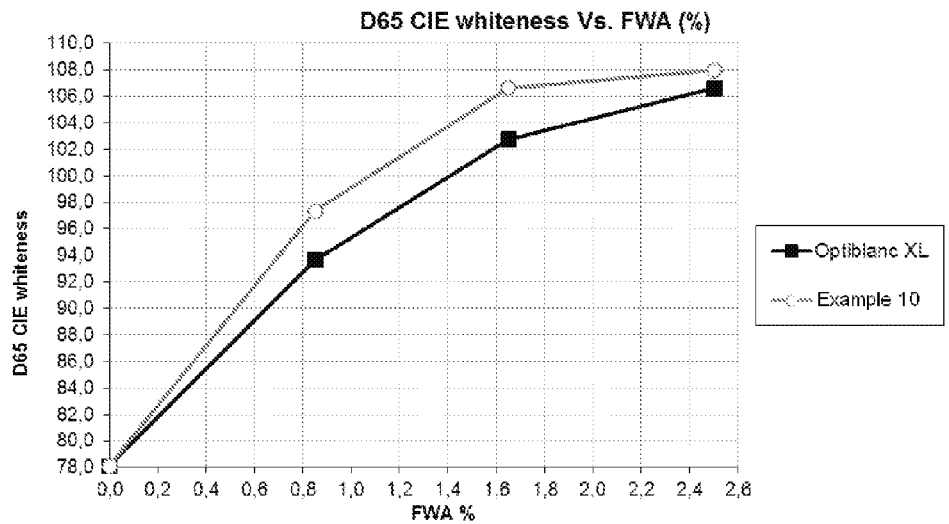
FIG. 1 shows the D65/10° CIE Whiteness values.

A novel class of 4,4'-aminostilbene-2,2'-disulphonic compounds has now been found which are useful as fluorescent whitening agents and have properties superior to those of the optical brighteners already known.

The optical brighteners according to the invention are obtained from particular secondary amines of type 2-(beta-aminopropionamido) alkanesulphonic acid and salts thereof, which are synthesised in turn with the Michael reaction between amines and unsaturated (meth)acrylamide-2-alkanesulphonic monomers and the salts thereof. Some of said amines are novel, and are an object of the invention.

The invention also relates to processes for synthesising said amino intermediates, the processes for synthesising the optical brighteners obtained from them, their aqueous solutions, their compositions for bleaching paper containing at least one binder or a pigment, the corresponding application methods for bleaching paper in the presence or absence of alkaline-earth metal salts, and the related uses.

The novel optical brighteners of the present invention provide very high performance in terms of the degree of fibre bleaching obtainable, in particular on cellulose, and especially on paper and cardboard. This means that, the required degree of whitening being equal, a smaller amount of optical brightener than for other optical brighteners already tested and known is sufficient. The resulting benefits are both financial and ecological.

The optical brighteners according to the present invention are represented by formula (I):

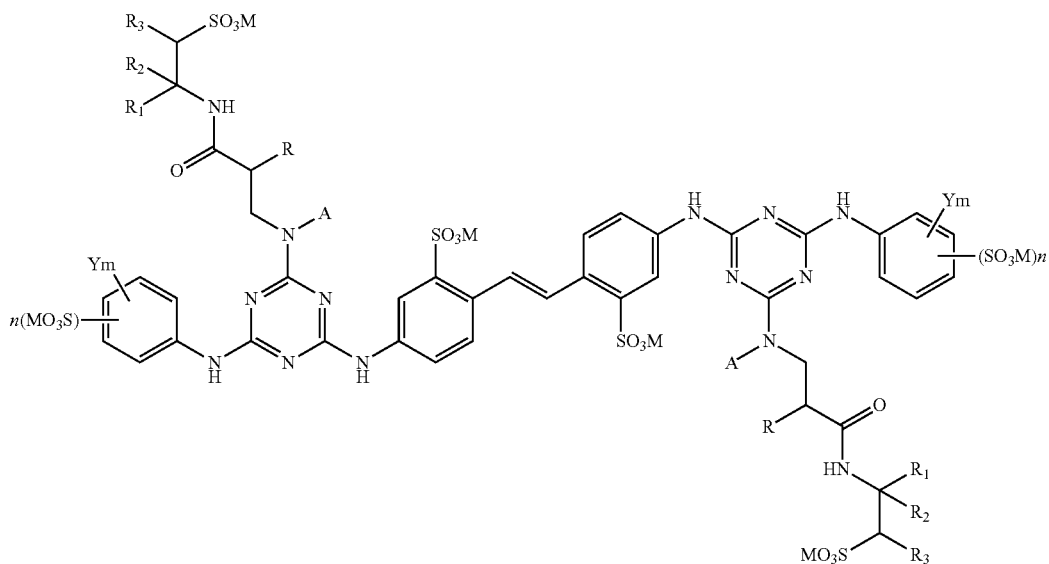

Formula (I)

wherein n is 0, 1 or 2;

Y is H, $C_1$-$C_4$ alkyl, LOOM, —CO—$CH_3$, —$SO_2$—$NH_2$, —CN;

m is 0.1 or 2;

R, $R_1$, $R_2$, $R_3$, which are the same or different, are H, methyl, ethyl;

the M groups are independently H, Li, Na, K, Ca, Mg, ammonium, protonated ions derived from alkyl amines, alkanolamines or alkylalkanolamines;

A is selected from the group comprising H, $C_1$-$C_8$ alkyl, $C_3$-$C_8$ cycloalkyl, $C_1$-$C_8$ hydroxyalkyl, alkoxyalkyl, phenyl, alkylphenyl, the side chain of a carboxylic or sulphonic amino acid wherein the carboxylic or sulphonic groups are salified with the M group as defined above, or the $SO_3M$ group, M being as defined above.

A can be, for example:

hydrogen, methyl, ethyl, propyl, butyl, 2-hydroxyethyl, 3-hydroxypropyl, 2-hydroxypropyl, 2-hydroxybutyl, 4-hydroxybutyl, 1,1-dimethyl-2-hydroxyethyl, 2-methoxyethyl or phenyl; or the side chain of an carboxylic amino acid salt such as the following radicals: —$CH_2COOM$ (glycine), —CH($CH_3$)COOM (alanine), —CH($CH_2OH$)COOM (serine), —CH(COOM)$CH_2CH(CH_3)_2$ (leucine), —CH(COOM)($CH_2)_4NH_2$ (lysine), —CH(COOM)$CH_2COOM$ (aspartic acid), —CH(COOM)($CH_2)_2$COOM (glutamic acid), or the radicals 2-(COOM)phenyl and 4-(COOM)phenyl, wherein M is as defined above; or the residue of a sulphonic amino acid salt, such as the —$SO_3M$ residue (sulphamic acid), —$CH_2CH_2SO_3M$ (taurine), 3-($SO_3M$)-phenyl (metanilic acid), 4-($SO_3M$)-phenyl (sulphanilic acid), 2,4-di($SO_3M$)-phenyl (2,4-aniline-disulphonic acid), 2,5-di($SO_3M$)-phenyl (2,5-aniline-disulphonic acid) or a residue of formula (II):

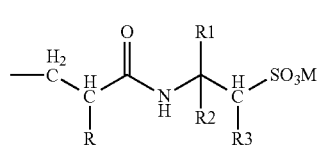

Formula (II)

wherein M, R, $R_1$, $R_2$ and $R_3$ are as defined above.

The invention also relates to the hydrated forms of the compounds of formula (I).

The amino intermediates according to the invention have the following formula (III):

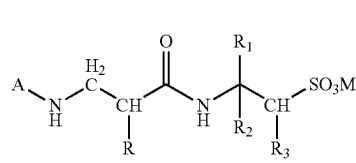

Formula (III)

wherein A, R, $R_1$, $R_2$ and M have the meanings defined above.

The amines of formula III are obtained by Michael addition reaction as follows:

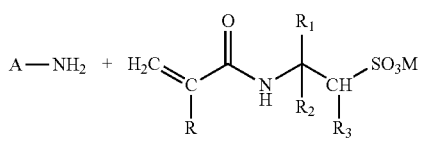

wherein

R, $R_1$, $R_2$, $R_3$ and M are as defined above and

A-$NH_2$ is $NH_3$, a $C_1$-$C_8$ primary alkyl amine, a $C_1$-$C_8$ primary cycloalkylamine, aniline, aromatic alkyl amine, an carboxylic or sulphonic amino acid or a salt thereof, or is a primary alkanolamine.

A-NH$_2$ can be, for example:
- an amine such as methylamine, ethylamine, propylamine, butylamine, ethanolamine, propanolamine, isopropanolamine, butanolamine, isobutanolamine or aniline; or
- a carboxylic amino acid such as glycine, alanine, serine, leucine, lysine, aspartic acid, glutamic acid, 2-aminobenzoic acid, 4-aminobenzoic acid and the salts thereof; or
- a sulphonic amino acid such as taurine, sulphamic acid, sulphanilic acid, metanilic acid, 2,5-aminobenzene disulphonic acid, 2,4-aminobenzene disulphonic acid, or the compound of formula (II).

Particularly preferred are the amines of formula (III) obtained by Michael reaction between primary alkanolamines or carboxylic or sulphonic amino acids and 2-acrylamido-2-methylpropane sulphonic acid and the salts thereof (AMPS).

AMPS (ATBS)—(CAS RN of the acid form 15214-89-8)

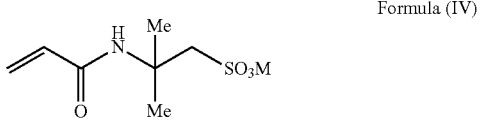

Formula (IV)

M is H, Li, Na, K, Ca, Mg, ammonium, protonated ions derived from alkyl amines or alkylalkanolamines or alkanolamines.

Most preferred are the amines of formula (III), obtained by Michael reaction between ethylamine, ethanolamine, isopropanolamine, alanine, aspartic acid, taurine and 2-acrylamido-2-methylpropane sulphonic acid and the salts thereof (AMPS).

The optical brighteners according to the invention are obtained by processes similar to those described, for example, in GB 896533. GB 1293804, U.S. Pat. No. 3,532, 692, U.S. Pat. No. 4,468,341, U.S. Pat. No. 6,210,449, WO 96/00221, EP 860437, EP 1378545.

For example, one mole of DAS can be reacted under suitable conditions, in succession, with 2 moles of cyanuryl chloride in the presence of water or solvents and proton acceptors or bases so that about 4 unreacted chlorine atoms remain on the triazine ring. This intermediate reactive species is reacted in turn in one or more steps with 2 moles of another amine and then with another 2 moles of a different amine. DAS, cyanuryl chloride and amines can obviously be reacted in different sequences, while still producing effective products. The well-known different reactivities of the three chlorine atoms of cyanuryl chloride to nucleophilic agents such as amines can be exploited in these syntheses.

To produce the optical brighteners of formula (I) of the invention, it is therefore necessary to introduce, in at least one step of this process, at least one amine of formula (III), preferably at least 2 moles of one or more amines of formula (III).

At the end of the reaction, the crude solution of the corresponding optical brightener can be desalted, for example, by suitable membrane separation methods, and concentrated as described, for example, in EP-A 992 547.

The preferred temperatures range between −10° C. and 150° C., more preferably between −10° C. and 100° C. The preferred synthesis pressures range between 0 and 2 bar.

The manufacturing process of the optical brighteners of formula I is a further object of the invention.

The preferred membrane separation methods are ultrafiltration, diffusion dialysis and electrodialysis. However, the resulting whitening agent can also be isolated as a solid, for example by direct drying, salting or acid addition. The solid formed can be isolated, for example, on a filter press and further purified by washing.

Aqueous solutions can also be prepared from the crude solutions or from concentrated, desalted solutions.

The concentrations of the solutions of optical brighteners are usually characterised by the parameter E1% 1 cm, which corresponds to the extinction value at the wavelength of maximum absorption of a solution containing 1% of the product in question, measured with a 1 cm optical path. The E1% 1 cm values of the solutions of the optical brighteners of the invention preferably range between 50 and 200.

The amines according to the invention are usually prepared with the Michael reaction shown in scheme 1, but other synthesis routes can also be used. The methods of preparing said amines are disclosed in GB 1329565, U.S. Pat. No. 4,985,591, U.S. Pat. No. 4,090,967 and U.S. Pat. No. 5,025,085.

The Michael reaction is preferably performed in a solvent, preferably aqueous, with stoichiometric amounts of the reagents, or also with an excess of amine A-NH$_2$. The reaction can also be carried out in the absence of solvents, in which case an excess of amine A-NH$_2$ is preferably used.

The solvents most commonly used for this reaction are water, methanol, ethanol, other alcohols, ketones, ethers, esters and hydrocarbons. The solvents can be used at reflux temperature or at lower temperatures.

The reaction temperatures preferably range between 0° C. and 150° C., more preferably between 20° C. and 100° C.

The reaction pressures can also exceed atmospheric pressure. However, it is usually necessary to apply pressure only if ammonia or volatile amines are used. The reaction can usually be effected at atmospheric pressure or up to 5 bar.

The molar ratio of amine A-NH$_2$ to the (meth)acrylamide-2-alkanesulphonic compound or a salt thereof is preferably at least 1:1. When an excess of amine A-NH$_2$ is used, it is usually eliminated at the end of the reaction by distillation, possibly under vacuum, or alternatively left to generate optical brighteners with mixed amino residues.

The compounds of formula (I) can be used in the detergent, paper and textile industries.

The aqueous solutions of the compounds of formula (I) are one object of the invention.

The compounds of formula (I) or the compositions containing them can be incorporated in compositions for optical brightening of cellulose, paper or cardboard substrates, which are a further object of the invention.

Said compositions for the surface treatment of paper such as coating or size press contain at least one compound of formula (I) as defined above, and:
- at least one synthetic or natural binder such as polyvinyl alcohol, styrene/butadiene and/or styrene/acrylate copolymers, vinyl acetate, possibly modified by introducing a third monomer such as acrylonitrile, acrylamide, acrylic acid, methacrylic acid, maleic acid, itaconic acid, vinyl chloride, vinyl esters or ethylene, alone or mixed together; starch, amylose, amylopectin, carboxymethylcellulose, hydroxyalkylcellulose or casein;
- optionally, a mineral pigment such as calcium carbonate, kaolin, talc, titanium dioxide, barium sulphate, aluminium hydroxide, satin white or mixtures thereof;
- optionally, other additives such as antifoaming agents, dyes, dispersing agents, fixation agents, divalent metal salts, crosslinking agents, sequestering agents and chelating agents, lubricants, pH correctors, biocides and preservatives, rheology and water retention modifiers;

water.

To obtain a particularly functional composition it is advantageous, if desired, to incorporate in the aqueous solutions a carrier substance, i.e. a substance whose addition further increases the efficiency of the optical brighteners and therefore produces an even greater degree of whiteness. Examples of carrier substances include polyglycols, polyvinyl alcohols, natural and modified starches.

The optical brighteners of the invention are particularly effective in the treatment of paper containing water-soluble alkaline-earth metal salts such as calcium chloride and magnesium chloride. In particular they are effective in the surface treatment of the paper used in ink-jet printers (ColorLok technology).

The compositions of the optical brighteners of the invention can be applied to paper on one or more occasions using any suitable method, such as metal blade, levelling roller, brush, air-knife, knife or compression coating, etc.

The coating can subsequently be immobilised and dried, first with hot air and/or IR irradiation and/or with steam-heated drying cylinders, and subsequently with hot calendering.

In one aspect thereof, the invention therefore relates to a method for fluorescent whitening of a cellulose, paper or cardboard substrate comprising placing the surface of said substrate in contact with a composition as defined above containing a compound of formula (I).

EXAMPLES

The concentrations of the optical brightener solutions are generally characterised by the parameter E1% 1 cm, which corresponds to the extinction value at the wavelength of maximum absorption of a solution containing 1% of the product in question, measured with a 1 cm optical path.

Preparation of Amino Compounds of Formula (III)

Example 1

AMPS-TAURINE (2-amino-ethanesulphonic acid)

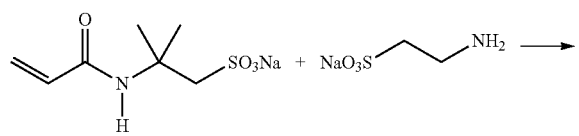

29.8 g of 30% NaOH and 25 g of demi water were added to a flask maintained at room temperature.

28 g of taurine was added in 30 minutes.

The flask was heated to 45-50° C., and 107 g of AMPS solution neutralised with NaOH (48% in water as sodium salt) was dropped therein in 2 h.

The temperature was maintained at 50° C. for 8 h.

The solution was characterised by NMR analysis.

An aliquot of said solution was dried to obtain a solid, and IR analysis was conducted.

The NMR and IR analyses confirmed that the taurine addition compound was identical to the AMPS sodium salt.

Example 2

AMPS-ASPARTIC ACID (2-amino-1,4-butanedioic acid)

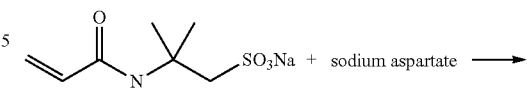

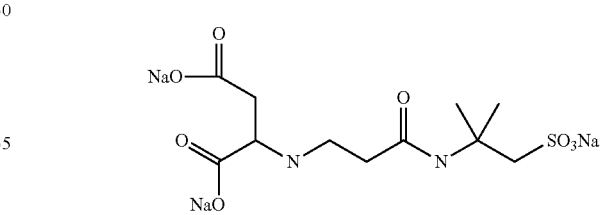

174.4 g of 30% NaOH was added to a flask maintained at room temperature, and 87.06 g of aspartic acid was added in 30 minutes while maintaining the temperature below 30° C.

The flask was heated to 70° C., and 312 g of AMPS sodium salt (48% conc.) was dropped therein in 2 h.

The temperature was maintained at 70° C. for 5 h.

The solution was characterised by NMR analysis.

An aliquot of said solution was dried to obtain a solid, and IR analysis was conducted.

The NMR and IR analyses confirmed that the sodium aspartate addition compound was identical to AMPS sodium salt.

Example 3

AMPS-Isopropanolamine

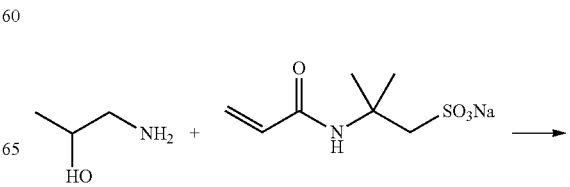

-continued

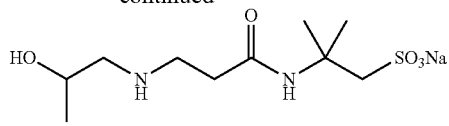

16.35 g of isopropanolamine was loaded into a flask maintained at 50° C.

104 g of AMPS-sodium (48%) was dropped therein in 2 h.

The temperature was maintained at 50° C. for 5 h.

The solution was characterised by NMR analysis.

An aliquot of said solution was dried to obtain a solid, and IR analysis was conducted.

The NMR and IR analyses confirmed that the monoisopropanolamine addition compound was identical to AMPS sodium salt.

Example: 4

AMPS-Mea

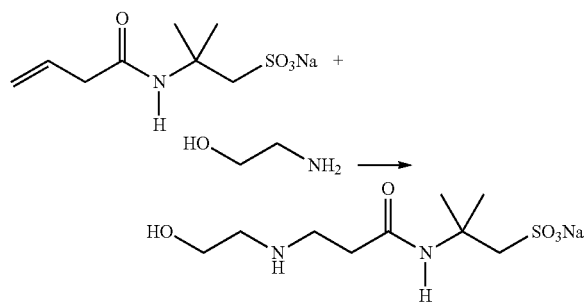

133.36 g of monoethanolamine (assay value 80%) was added to a flask maintained at 45° C.

137 g of sodium AMPS (concentration 50%) was dropped therein in 2 h, and the temperature was maintained at 50° C. for 2 h.

The water and excess monoethanolamine were distilled off, reaching 4 mmHg and 117° C.

120 g of water was added.

A solution was obtained with 41% of the product.

The solution was characterised by NMR analysis.

NMR analysis confirmed that the monoethanolamine addition compound was identical to AMPS sodium salt.

Example 5

AMPS-2-ethylhexylamine 57.5 g of 2-ethylhexylamine (assay value 98%) was added to a flask maintained at 50° C.

208 g of sodium AMPS (concentration 48%) was dropped therein in 2 h, and the temperature was maintained at 50° C. for 8 h.

The solution was characterised by NMR analysis.

NMR analysis confirmed that the 2-ethylhexylamine addition compound was identical to AMPS sodium salt.

Example 6

AMPS-Aniline 20.3 g of aniline was added to a flask maintained at 100° C.

110.2 g of sodium AMPS (concentration 45%) was dropped therein in 2 h, the temperature was maintained at 100° C. for 18 h, and the pH was maintained at >11 with NaOH.

The solution was characterised by NMR analysis.

NMR analysis confirmed that the aniline addition compound was identical to AMPS sodium salt.

Preparation of Dichloro Intermediates for Synthesis of the Novel Optical Brighteners Example 7

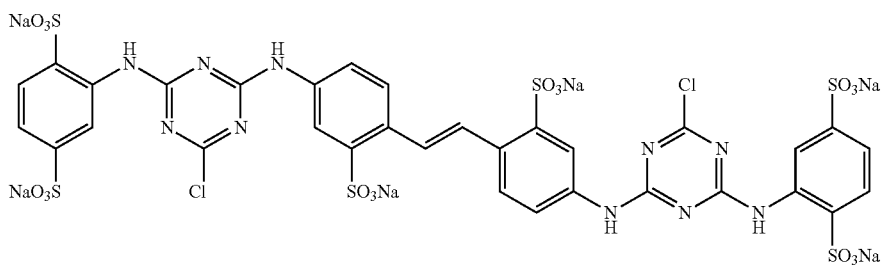

60 g of cyanuryl chloride was dispersed in 350 g of water maintained at between 0 and 20° C.

288.4 g of a 28.8% solution of 2-5 sodium aniline disulphonate was dripped into said dispersion in 30-90 mins.

During dripping, the pH was maintained at between 2 and 4 using an Na$_2$CO3 solution.

After dripping, the solution was maintained at between 10 and 20° C. for about 4 h.

This solution was dripped, in 1-2 h, into a flask containing 57.84 g of DAS, 166 g of water and 16.66 g of carbonate.

During dripping, the pH was maintained at between 6 and 8 with an Na2CO3 solution.

The temperature was maintained at 20° C. for about 1 h.

The solution was heated in 1 h to 40-60° C., and maintained for about 1-2 h, to obtain product 7 in the form of an aqueous solution.

Example 8

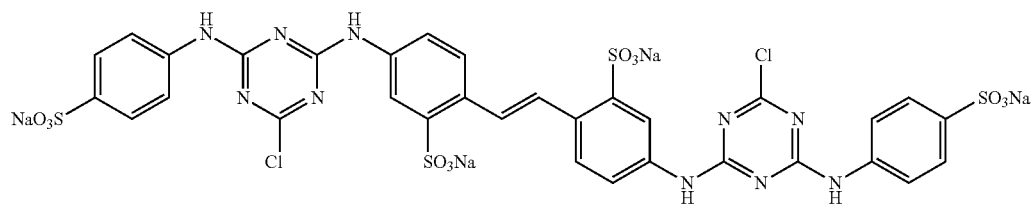

60 g of cyanuryl chloride was dispersed in 333 g of water maintained at between 0 and 20° C.

320.6 gm of a 17.4% solution (as acid) of sodium sulphanilate was dripped into said dispersion in 30-90 mins During dripping, the pH was maintained at between 2 and 4 using an Na$_2$CO3 solution.

After dripping, the solution was maintained at between 10 and 20° C. for about 4 h.

Said solution was dripped, in 1-2 h, into a flask containing 59.23 g of DAS, 250 g of water and 16.66 g of carbonate.

During dripping, the pH was maintained at between 6 and 8 with an Na$_2$CO3 solution.

The temperature was maintained at 20° C. for about 1 h.

The solution was heated in 1 h to 40-60° C., and maintained for about 1-2 h, to obtain product 8 in the form of an aqueous solution.

Example 9

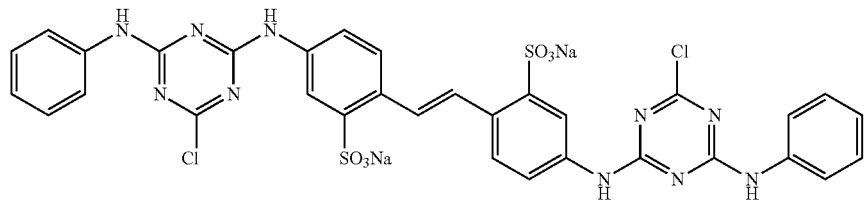

59.4 g of cyanuryl chloride was reacted with 59.7 g of DAS at between −10° C. and +10° C. in a 35% solution of aqueous acetone, in the presence of sodium bicarbonate.

At the end of the reaction the dispersion obtained was reacted with 27.12 g of aniline at temperatures ranging between 20 and 40° C., and the pH was controlled by adding aqueous soda between 4 and 8?? for about 30 minutes.

Product 9 was obtained in the form of a dispersion or slurry in water/acetone solution.

Preparation of Optical Brighteners of Formula (I)

Example 10

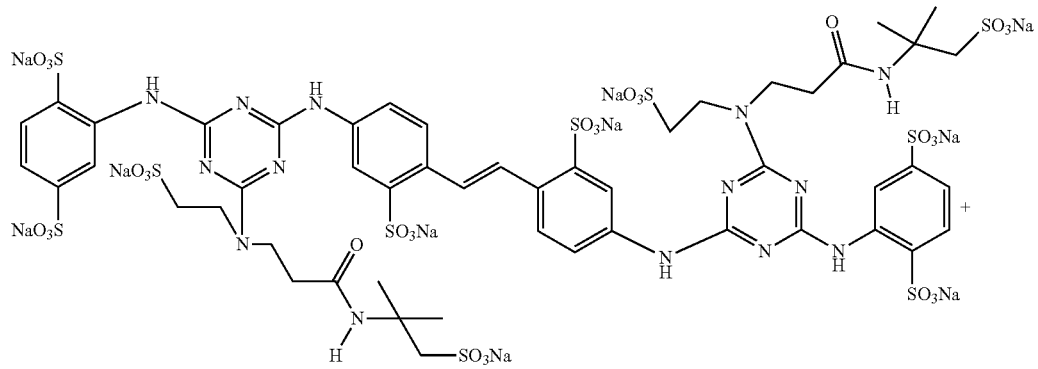

429 g of aqueous solution containing 0.3822 moles of the AMPSNa-TaurineNA adduct described in example 1 was added to 1000 g of the aqueous solution of example 7, containing 0.1563 moles of intermediate 7.

The mixture was heated to 90-100° C., and maintained at that temperature for 2 h.

The pH was maintained at between 8 and 10 with sodium carbonate.

1550 g of solution containing the optical brightener having an $E^{1\%}_{1cm}$ value of 60 was discharged.

The solution was clarified by filtration and concentrated by osmosis.

1320 g of aqueous solution of optical brightener 10 with an extinction coefficient $E_{11}$ of 68 was obtained.

Part of the solution was acidified to pH 1 with HCl.

The resulting dispersion of solid acid product was filtered and dried.

The resulting powder corresponded to the acid form of the optical brightener.

The powder of the form acid was dispersed again in water and neutralised with different bases, such as sodium hydroxide, potassium hydroxide and dimethylaminoethanol, reconstituting the solutions of the respective salts. Said aqueous bases were also used in mixtures to neutralise the acid form, thus obtaining aqueous solutions of mixed salts of optical brightener.

Example 11

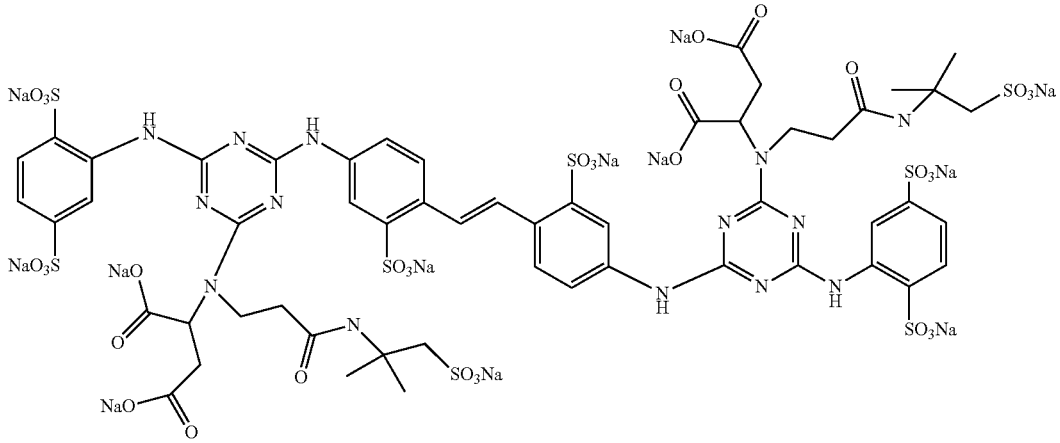

412 g of aqueous solution containing 0.43 moles of the AMPSNa-sodium aspartate adduct described in example 2 was added to 1000 g of the aqueous solution of example 7, containing 0.1563 moles of intermediate 7.

The mixture was heated to 90-100° C., and maintained at that temperature for 2 h.

The pH was maintained at between 8 and 10 with sodium carbonate.

An aqueous solution containing optical brightener 11 was obtained.

The solution was clarified by filtration, and extinction coefficient $E^{1\%}_{1cm}$ was adjusted to 68 by osmosis.

Example 12

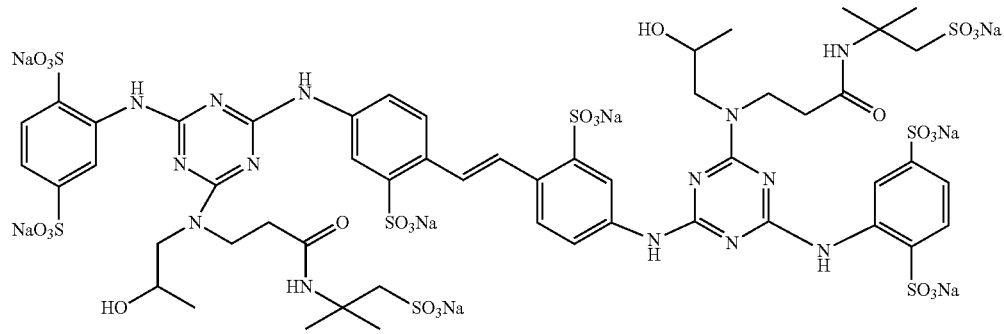

255 g of aqueous solution of the adduct described in example 3 was added to 1000 g of the aqueous solution of example 7, containing 0.1563 moles of intermediate 7.

The mixture was heated to 90-100° C., and maintained at that temperature for 2 h.

The pH was maintained at between 8 and 10 with sodium carbonate.

An aqueous solution containing optical brightener 12 was obtained.

The solution was clarified by filtration, and extinction coefficient $E^{1\%}_{1cm}$ was adjusted to 68 by osmosis.

Example 13

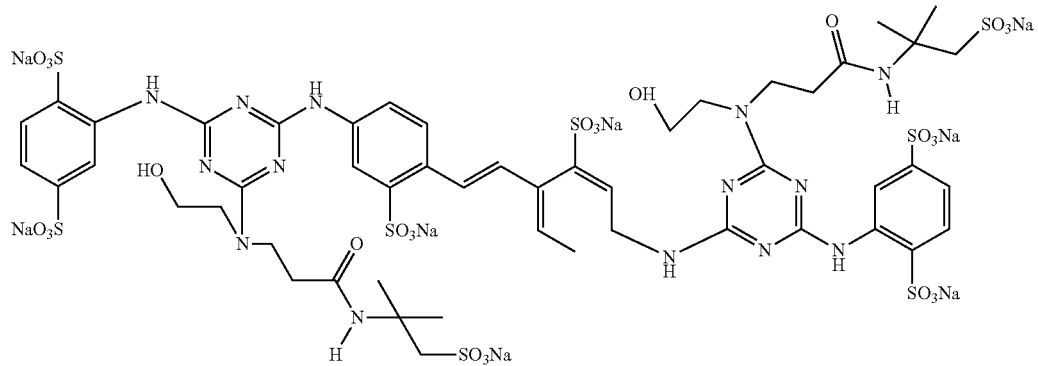

197 g of aqueous solution of the adduct described in example 4 was added to 1000 g of the aqueous solution of example 7, containing 0.1563 moles of intermediate 7.

The mixture was heated to 90-100° C., and maintained at that temperature for 2 h.

The pH was maintained at between 8 and 10 with sodium carbonate.

An aqueous solution containing optical brightener 13 was obtained.

The solution was clarified by filtration, and extinction coefficient $E^{1\%}_{1cm}$ was adjusted to 68 by osmosis.

Example 14

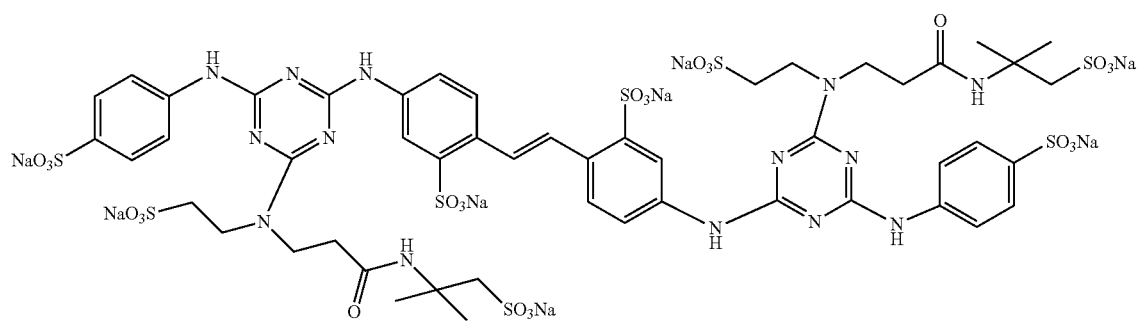

429 g of aqueous solution containing 0.3822 moles of AMPSNa-TaurineNA adduct described in example 1 was added to 950 g of the aqueous solution of example 8, containing 0.1563 moles of intermediate 8.

The mixture was heated to 90-100° C., and maintained at that temperature for 2 h.

The pH was maintained at between 8 and 10 with sodium carbonate.

The solution was clarified by filtration and concentrated by osmosis. An aqueous solution of optical brightener 14 with an extinction coefficient $E^{1\%}_{1cm}$ of 114 was obtained.

Example 15

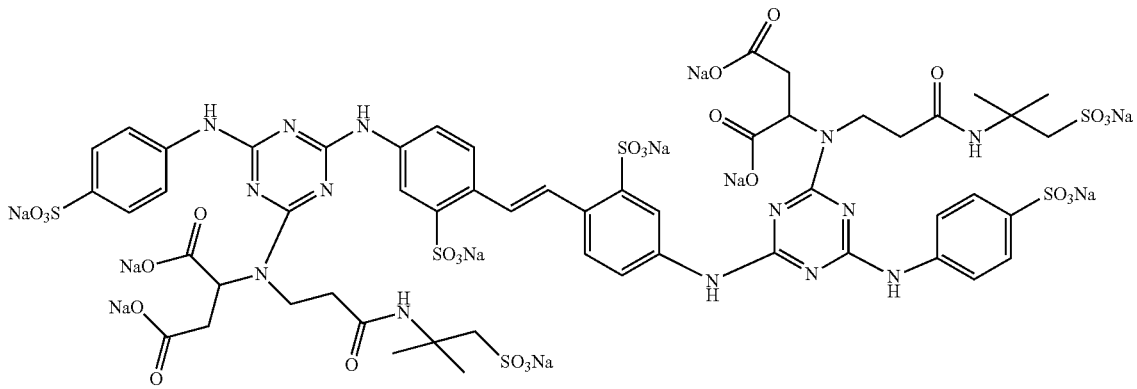

412 g of aqueous solution containing 0.43 moles of the AMPSNa-sodium aspartate adduct described in example 2 was added to 950 g of the aqueous solution of example 8, containing 0.1563 moles of intermediate 8.

The mixture was heated to 90-100° C., and maintained at that temperature for 2 h.

The pH was maintained at between 8 and 10 with sodium carbonate.

An aqueous solution containing optical brightener 15 was obtained.

The solution was clarified by filtration, and extinction coefficient $E^{1\%}_{1cm}$ was adjusted to 114 by osmosis.

Example 16

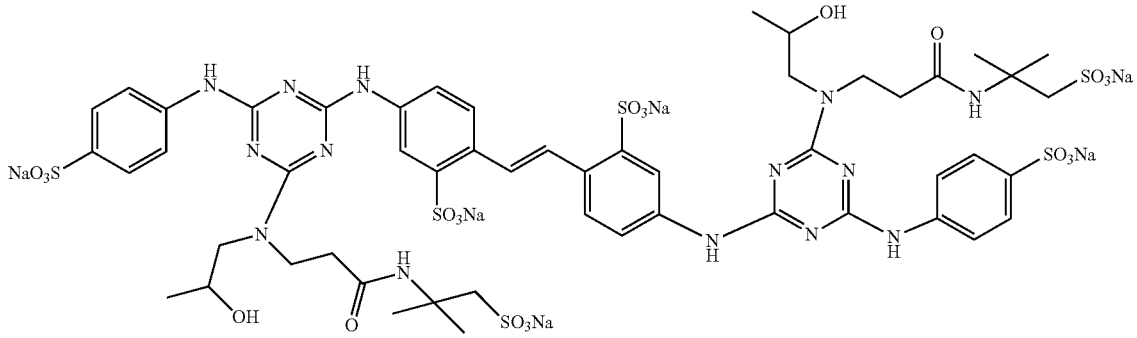

255 g of aqueous solution of the adduct described in example 3 was added to 950 g of the aqueous solution of example 8, containing 0.1563 moles of intermediate 8.

The mixture was heated to 90-100° C., and maintained at that temperature for 2 h.

The pH was maintained at between 8 and 10 with sodium carbonate.

An aqueous solution containing optical brightener 16 was obtained.

The solution was clarified by filtration, and extinction coefficient $E^{1\%}_{1cm}$ was adjusted to 114 by osmosis.

Example 17

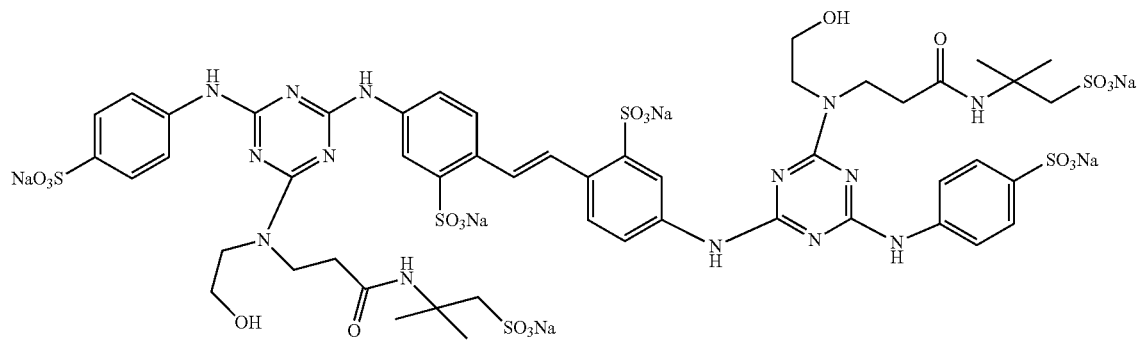

197 g of aqueous solution of the adduct described in example 4 was added to 950 g of the aqueous solution of example 8, containing 0.1563 moles of intermediate 8.

The mixture was heated to 90-100° C., and maintained at that temperature for 2 h.

The pH was maintained at between 8 and 10 with sodium carbonate.

An aqueous solution containing optical brightener 17 was obtained.

The solution was clarified by filtration, and extinction coefficient $E^{1\%}_{1cm}$ was adjusted to 114 by osmosis.

Example 18

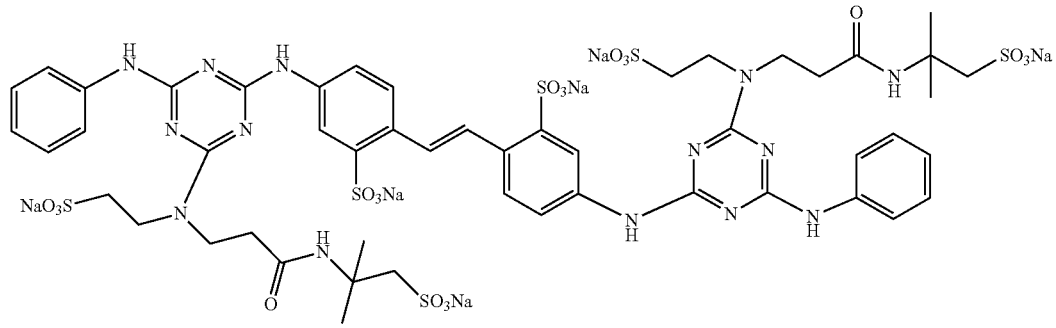

429 g of aqueous solution containing 0.3822 moles of the AMPSNa-TaurineNa adduct described in example 1 was added to 900 g of the dispersion of example 9, containing 0.1563 moles of intermediate 9.

The mixture was heated to 90-100° C., eliminating the acetone by distillation.

The pH was maintained at between 8 and 10 with sodium carbonate.

The resulting slurry or dispersion was filtered, and the panel washed with a 10% aqueous solution of NaCl.

The precipitate was dried, and a solid corresponding to optical brightener 18 was obtained.

Example 19

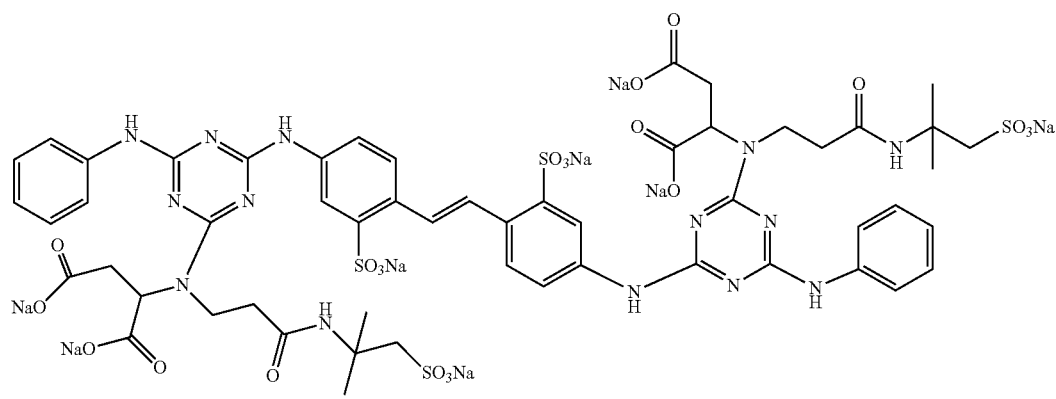

412 g of aqueous solution containing 0.43 moles of AMPSNa-sodium aspartate adduct described in example 2 was added to 900 g of the dispersion of example 9, containing 0.1563 moles of intermediate 9.

The mixture was heated to 90-100° C., and the acetone was eliminated by distillation.

The pH was maintained at between 8 and 10 with sodium carbonate.

The resulting slurry or dispersion was filtered, and the panel washed with a 10% aqueous solution of NaCl.

The precipitate was dried, and a solid corresponding to optical brightener 19 was obtained.

Example 20

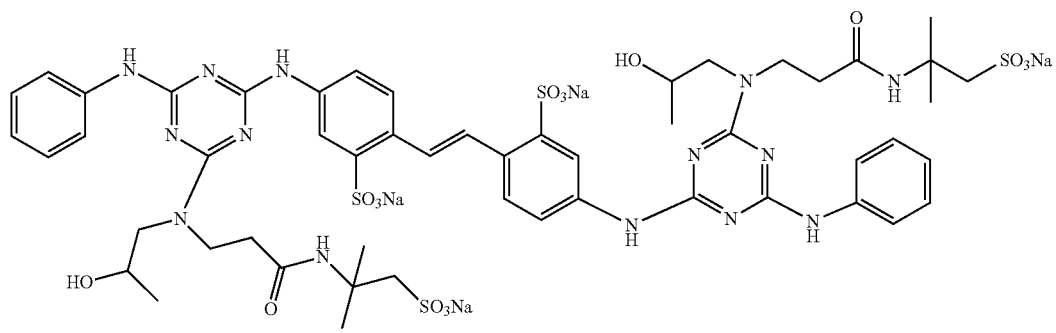

255 g of aqueous solution of the adduct described in example 3 was added to 900 g of the dispersion of example 9, containing 0.1563 moles of intermediate 9.

The mixture was heated to 90-100° C., and the acetone was eliminated by distillation.

The pH was maintained at between 8 and 10 with sodium carbonate.

A sufficient amount of sodium chloride was added to the solution to form 2 phases, and the organic phase was recovered.

The organic phase was adjusted to the assay value using a 4:1 w/w water and urea solution.

A water/urea solution containing optical brightener 20 with an extinction coefficient $E^{1\%}_{1cm}$ of 120 was obtained.

Example 21

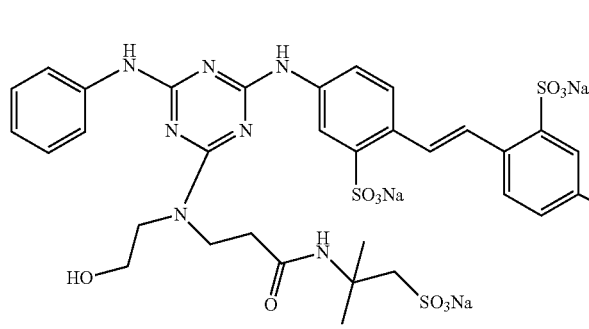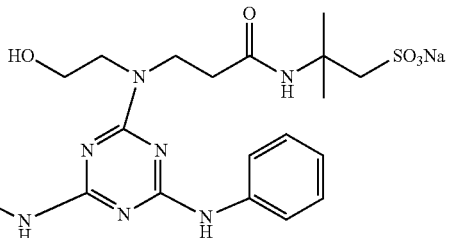

197 g of aqueous solution of the adduct described in example 4 was added to 900 g of the dispersion of example 9, containing 0.1563 moles of intermediate 9.

The mixture was heated to 90-100° C., eliminating the acetone by distillation, and maintained at that temperature for 2 h.

The pH was maintained at between 8 and 10 with sodium carbonate.

A sufficient amount of sodium chloride was added to the solution to form 2 phases, and the organic phase was recovered.

The organic phase was adjusted to the assay value using a 4:1 w/w water and urea solution.

A solution of water/urea and optical brightener 21 with an extinction coefficient $E^{1\%}_{1cm}$ of 120 was obtained.

Example 22

By proceeding similarly to the process described in example 10 and using 0.3822 moles of the compound of formula (III) of example 5 instead of the compound of example 1, optical brightener 22 was obtained.

Example 23

By proceeding similarly to the process described in example 10 and using 0.3822 moles of the compound of formula (III) of example 6 instead of the compound of example 1, optical brightener 23 was obtained.

Application examples for evaluation of the novel optical brighteners.

Commercial optical brighteners which are among the best on the market for the applications indicated were used for the application comparisons.

In particular the following were used:

Optiblanc XL (3V Sigma Spa)—stilbene hexasulphonate optical brightener—with extinction coefficient $E^{1\%}_{1cm}$ of 68

Leucophor SAC (Clariant)—stilbene hexasulphonate optical brightener—with an extinction coefficient $E^{1\%}_{1cm}$ of 70—specifically diluted with water to an $E^{1\%}_{1cm}$ of 68 for the examples.

Optiblanc SLK (3V Sigma SpA)—stilbene tetrasulphonate optical brightener—with an extinction coefficient $E^{1\%}_{1cm}$ of 114

Blankophor NC (Blankophor Gmbh)—stilbene optical brightener—with an extinction coefficient $E^{1\%}_{1cm}$ of 125—specifically diluted with water to an $E^{1\%}_{1cm}$ of 114 for the examples.

Optiblanc AFW/S (3V Sigma SpA)—stilbene tetrasulphonate optical brightener—with an extinction coefficient $E^{1\%}_{1cm}$ of 81

All the application comparisons of the examples were conducted with the same $E^{1\%}_{1cm}$ extinction values as the formulations.

Example 24

Paper Coating Application—Example 10 vs. XL

A paper coating composition having the following recipe:

| | | |
|---|---|---|
| Calcium carbonate | Hydrocarb 90 AV (Omya) | 80 parts |
| Kaolin | Capim DG slurry (Imerys) | 20 parts |
| Synthetic binder | Litex P7110 (PolymerLatex) | 12 parts |
| Carboxymethylcellulose | Finnfix 10 (CPKelco) | 0.6 parts |
| NaOH (10% sol.) | up to pH = 9 | |
| Demineralised water | up to final dry residue = 65.0 | | was divided into 7 parts; one was left unchanged, without optical brightener, while 0.85%, 1.65% and 2.50% by weight of the Optiblanc XL optical brighteners and the optical brightener of example 10 respectively was added to the others.

After 5 minutes' stirring, each sample was applied to "Fabriano 2 smooth" backing paper with a Sheen 1133N automatic applicator equipped with a 1140/32/10 wire bar.

At the end of the application the specimens were dried at room temperature for 1 hour.

Table 1 below shows the optical properties detected by an ELREPHO LWE450-X reflectometer.

TABLE 1

| sample | dose % | D65/10° brightness | D65/10° CIE whiteness | L* | a* | b* |
|---|---|---|---|---|---|---|
| Optiblanc XL | 0.00 | 87.6 | 78.13 | 96.54 | 0.18 | 2.95 |
| | 0.85 | 92.7 | 93.64 | 96.84 | 0.95 | −0.31 |
| | 1.65 | 96.0 | 102.74 | 97.15 | 1.29 | −2.24 |
| | 2.50 | 97.9 | 106.58 | 97.34 | 1.19 | −3.00 |
| Example 10 | 0.00 | 87.6 | 78.13 | 96.54 | 0.18 | 2.95 |
| | 0.85 | 93.7 | 97.33 | 96.97 | 1.17 | −1.11 |
| | 1.65 | 97.2 | 106.62 | 97.16 | 1.53 | −3.10 |
| | 2.50 | 98.2 | 107.94 | 97.34 | 1.25 | −3.31 |

The annexed FIG. 1 graphically illustrates the D65/10° CIE Whiteness values.

The application yield of the various brightening agents is quantifiable by the increase in the whiteness of the paper after the application of the composition; the optical brightener of example 10 clearly gave a better application yield, dose being equal.

Example 25

Application in Size Press—Example 10 vs. XL

A solution for surface treatment of paper in a size press, consisting of a Cargill C*Film 07311 corn starch paste with final dry residue of 7.0%, was divided into 7 parts;

one portion was left as is (i.e. unchanged for reference, with the dose of optical brightener=0), while the other portions were mixed respectively with:

20.85, 40.82 or 59.96 grams/liter of Optiblanc XL and the optical brightener of example 10.

After 5 minutes' stirring, each sample was applied to "Fabriano 2 smooth" backing paper with a laboratory doctor blade; at the end of the application the specimens were dried at room temperature for one hour.

The whiteness values found on the laboratory samples are set out in table 2 below.

TABLE 2

| sample | dose (g/l) | D65 brightness | D65 CIE whiteness | L* | a* | b* |
|---|---|---|---|---|---|---|
| Optiblanc XL | 0.00 | 94.9 | 102.08 | 96.85 | 1.65 | −2.24 |
| | 20.85 | 105.0 | 127.82 | 97.82 | 2.95 | −7.60 |
| | 40.82 | 107.4 | 132.38 | 98.07 | 2.96 | −8.52 |
| | 59.96 | 108.2 | 132.67 | 98.16 | 2.79 | −8.54 |
| Example 10 | 0.00 | 94.9 | 102.08 | 96.85 | 1.65 | −2.24 |
| | 20.85 | 105.2 | 128.30 | 97.80 | 3.09 | −7.72 |
| | 40.82 | 107.4 | 134.01 | 97.95 | 3.29 | −8.96 |
| | 59.96 | 108.7 | 136.45 | 98.10 | 3.28 | −9.45 |

Figure 2:
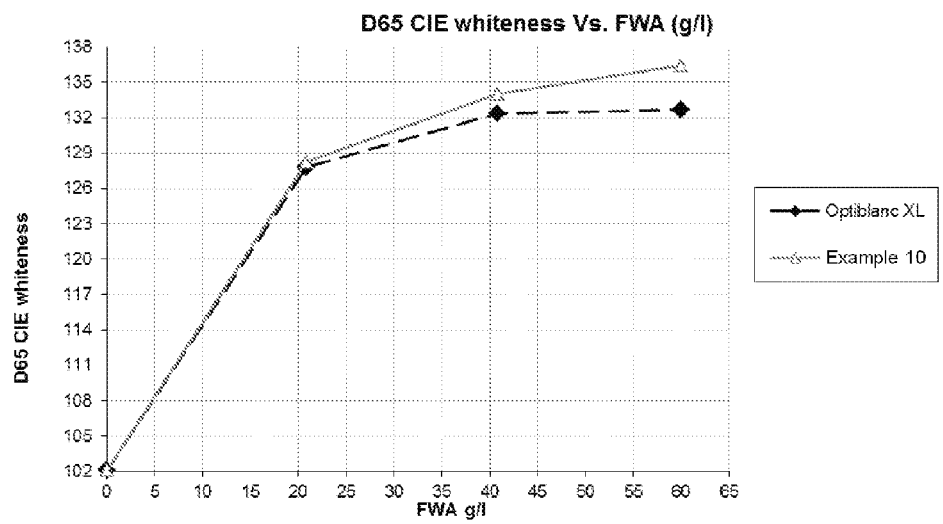
FIG. 2 shows the D65/10° CIE Whiteness values.

The annexed FIG. 2 graphically illustrates the D65/10° CIE Whiteness values.

Once again, the optical brightener of example 10 clearly gave a better application yield, dose being equal.

Example 26

Application in Color Lok—Example 10 v. XL 22 grams/liter of calcium chloride was added to a solution for surface treatment of paper in a size press, consisting of a Cargill C*Film 07311 corn starch paste with final dry residue of 6.5%, and the resulting mixture was divided into 7 parts;

one portion was left as is (i.e. unchanged for reference, with the dose of optical brightener=0), while the other portions were mixed respectively with:

10.43, 20.66 or 30.71 grams/liter of Optiblanc XL and the optical brightener of example 10.

After 5 minutes' stirring, each sample was applied to "Fabriano 2 smooth" backing paper with a laboratory doctor blade; at the end of the application the specimens were dried at room temperature for one hour.

The whiteness values found on the laboratory samples are set out in table 3 below:

TABLE 3

| sample | Dose (g/l) | D65 brightness | D65 CIE whiteness | L* | a* | b* |
|---|---|---|---|---|---|---|
| Optiblanc XL | 0.00 | 96.3 | 103.25 | 97.41 | 1.62 | −2.21 |
| | 10.43 | 102.7 | 121.11 | 97.80 | 2.60 | −6.07 |
| | 20.66 | 105.2 | 127.00 | 98.05 | 2.73 | −7.30 |
| | 30.71 | 105.9 | 127.93 | 98.10 | 2.64 | −7.48 |
| Example 10 | 0.00 | 96.3 | 103.25 | 97.41 | 1.62 | −2.21 |
| | 10.43 | 102.9 | 121.67 | 97.85 | 2.64 | −6.17 |
| | 20.66 | 105.4 | 127.44 | 98.06 | 2.84 | −7.39 |
| | 30.71 | 106.3 | 130.10 | 98.10 | 2.91 | −7.98 |

Figure 3:
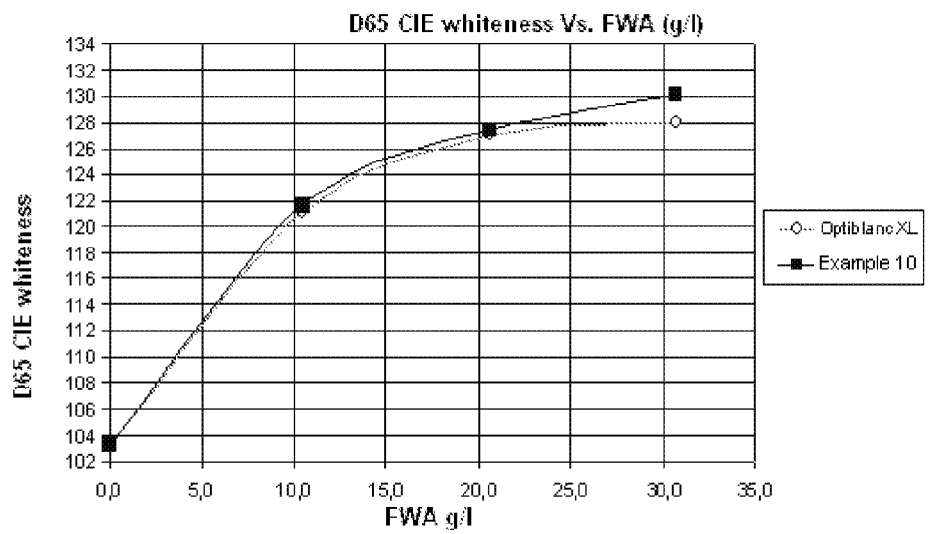
FIG. 3 shows the D65/10° CIE Whiteness values.

The annexed FIG. 3 graphically illustrates the D65/10° CIE Whiteness values.

The optical brightener of example 10 again clearly gave a better application yield, dose being equal, in the presence of calcium chloride.

Example 27

Application in Color Lok—Examples 11, 12 and 13 vs. XL and SAC

A paper coating composition having the following recipe:

| | | |
|---|---|---|
| Calcium carbonate | Hydrocarb 90 AV (Omya) | 85 parts |
| Kaolin | Capim DG slurry (Imerys) | 15 parts |
| Synthetic binder | Litex P7110 (PolymerLatex) | 10 parts |
| Starch | C*Icoat 07520 (Cargill) | 2 parts |
| Carboxymethylcellulose | Finnfix 10 (CPKelco) | 0.3 parts |
| NaOH (10% sol.) | up to pH = 9 | |
| Demineralised water | up to final dry residue = 60.0 | | was divided into 6 parts; one was left unchanged, without optical brightener, while 2.50% by weight respectively of the Optiblanc XL and Leucophor SAC optical brighteners and those of examples 11, 12 and 13 was added to the others.

After 5 minutes' stirring, each sample was applied to "Fabriano 2 smooth" backing paper with a laboratory doctor blade. At the end of the application the specimens were dried at room temperature for 1 hour.

Table 4 below shows the optical properties detected by an ELREPHO LWE450-X reflectometer.

TABLE 4

| sample | FWA % dose | D65/10° brightness | D65/10° CIE whiteness | L* | a* | b* |
|---|---|---|---|---|---|---|
| coating only | 0.00 | 88.8 | 81.40 | 96.66 | 0.31 | 2.28 |
| Optiblanc XL | 2.50 | 97.0 | 104.25 | 97.46 | 1.25 | −2.41 |
| Leucophor SAC | 2.50 | 96.8 | 103.59 | 97.44 | 1.20 | −2.27 |
| Example 11 | 2.50 | 98.9 | 108.63 | 97.55 | 1.36 | −3.36 |
| Example 12 | 2.50 | 98.2 | 106.51 | 97.61 | 1.18 | −2.84 |
| Example 13 | 2.50 | 97.7 | 106.57 | 97.42 | 1.42 | −2.96 |

The optical brighteners of examples 11, 12 and 13 clearly gave a better application yield than the comparators, dose being equal.

Example 28

Application in Size Press—Examples 11, 12 vs. XL

A solution for surface treatment of paper in a size press, prepared according to the recipe described in example 25, was divided into 4 parts;

one portion was left as is (i.e. unchanged for reference, with the dose of optical brightener=0), while the other portions were mixed respectively with 59.96 grams/liter of the following optical brighteners: Optiblanc XL, examples 11 and 12.

After 5 minutes' stirring, each sample was applied to "Fabriano 2 smooth" backing paper with a laboratory doctor blade; at the end of the application the specimens were dried at room temperature for one hour.

The whiteness values found on the laboratory samples are set out in table 5 below:

TABLE 5

| sample | dose of optical brightener (g/l) | D65 brightness | D65 CIE whiteness | L* | a* | b* |
|---|---|---|---|---|---|---|
| starch only | 0.00 | 94.9 | 102.08 | 96.85 | 1.65 | −2.24 |
| Optiblanc XL | 59.96 | 108.2 | 132.67 | 98.16 | 2.79 | −8.54 |
| Example 11 | 59.96 | 108.5 | 135.01 | 98.15 | 3.18 | −9.09 |
| Example 12 | 59.96 | 108.6 | 134.09 | 98.20 | 2.95 | −8.85 |

Example 29

Coating Application Test, Examples 14 and 16 vs. SLK

A paper coating composition having the recipe described in example 24 was divided into 10 parts; one was left unchanged, without optical brightener, while 0.40%, 0.80% and 1.20% by weight of the Optiblanc XLK optical brighteners and those of examples 14 and 16 respectively was added to the others.

After 5 minutes' stirring, each sample was applied to "Fabriano 2 smooth" backing paper with a Sheen 1133N automatic applicator equipped with a 1140/32/10 wire bar.

At the end of the application the specimens were dried at room temperature for 1 hour.

Table 6 below shows the optical properties detected by an ELREPHO LWE450-X reflectometer.

TABLE 6

| FWA sample | Dose FWA % | D65/10° brightness | D65/10° CIE whiteness | L* | a* | b* |
|---|---|---|---|---|---|---|
| Optiblanc SLK | 0.00 | 87.6 | 78.13 | 96.54 | 0.18 | 2.95 |
| | 0.40 | 92.6 | 93.32 | 96.95 | 0.91 | −0.22 |
| | 0.80 | 95.2 | 99.69 | 97.18 | 1.02 | −1.53 |
| | 1.20 | 96.1 | 101.07 | 97.33 | 0.85 | −1.76 |
| Example 14 | 0.00 | 87.6 | 78.13 | 96.54 | 0.18 | 2.95 |
| | 0.40 | 93.6 | 96.79 | 97.06 | 1.04 | −0.94 |
| | 0.80 | 96.3 | 103.49 | 97.27 | 1.19 | −2.34 |
| | 1.20 | 96.8 | 103.54 | 97.42 | 0.70 | −2.27 |
| Example 16 | 0.00 | 87.6 | 78.13 | 96.54 | 0.18 | 2.95 |
| | 0.40 | 93.2 | 95.50 | 96.99 | 1.03 | −0.69 |
| | 0.80 | 96.1 | 103.94 | 97.22 | 1.34 | −2.47 |
| | 1.20 | 97.0 | 104.98 | 97.36 | 1.08 | −2.63 |

Figure 4:
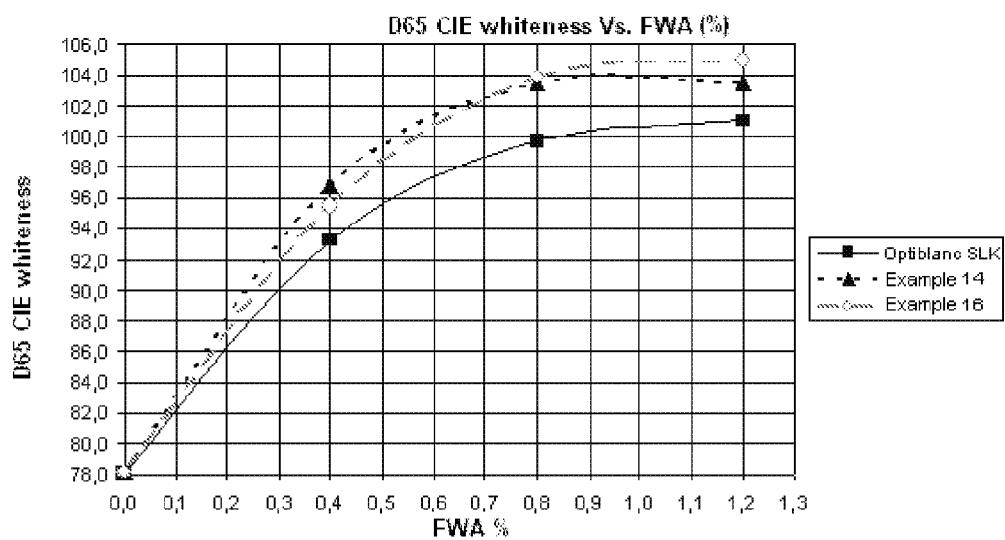
FIG. 4 shows the D65/10° CIE Whiteness values.

The annexed FIG. 4 graphically illustrates the D65/10° CIE Whiteness values.

Example 30

Coating Application Test, Examples 14 vs. Blankophor NC

A paper coating composition having the following recipe:

| Calcium carbonate | Hydrocarb 90 AV (Omya) | 100 parts |
| Synthetic binder | Styronal D517 (BASF) | 9 parts |
| Polyvinyl alcohol | Mowiol 4-98 (Kuraray Europe) | 0.6 parts |
| Carboxymethylcellulose | Finnfix 30 (CPKelco) | 0.2 parts |
| NaOH (10% sol.) | up to pH = 9 | |
| Demineralised water | up to final dry residue = 65.0 | | was divided into 9 parts; one was left unchanged, without optical brightener, while 0.30%, 0.60%, 0.90% and 1.20% by weight of the Blankophor NC optical brighteners and that of Example 14 respectively was added to the others.

After 5 minutes' stirring, each sample was applied to "Fabriano 2 smooth" backing paper with a laboratory doctor blade.

At the end of the application the specimens were dried at room temperature for 1 hour.

Table 7 below shows the optical properties detected by an ELREPHO LWE450-X reflectometer

TABLE 7

| sample | % dose | D65 brightness R457+ | D65 CIE whiteness | L* | a* | b* |
|---|---|---|---|---|---|---|
| Blancophor NC | 0.00 | 92.4 | 90.37 | 97.35 | 0.72 | 0.66 |
| | 0.30 | 95.5 | 99.26 | 97.60 | 1.18 | −1.20 |
| | 0.60 | 97.4 | 104.44 | 97.76 | 1.38 | −2.29 |
| | 0.90 | 98.5 | 107.19 | 97.86 | 1.43 | −2.86 |
| | 1.20 | 99.0 | 108.30 | 97.94 | 1.39 | −3.07 |
| Example 14 | 0.00 | 92.4 | 90.37 | 97.35 | 0.72 | 0.66 |
| | 0.30 | 96.0 | 101.34 | 97.65 | 1.34 | −1.65 |
| | 0.60 | 98.2 | 106.87 | 97.80 | 1.57 | −2.82 |
| | 0.90 | 99.2 | 109.03 | 97.92 | 1.51 | −3.25 |
| | 1.20 | 99.7 | 110.12 | 98.04 | 1.33 | −3.43 |

The optical brightener of example 14 clearly gave a better application yield, dose being equal.

Example 31

Application Test in Size Press; Examples 14 and 16 vs. AFW/S

A solution for surface treatment of paper in a size press, consisting of a Cargill C*Film 07319 corn starch paste with final dry residue of 10.0%, was divided into 10 parts; one portion was left as is (i.e. unchanged for reference, with the dose of optical brightener=0), while the other portions were mixed respectively with:

6.53, 12.95 or 19.25 grams/liter of Optiblanc AFW/S and the optical brighteners of example 14 and example 16, specifically diluted with water to obtain the same extinction coefficient $E^{1\%}_{1cm}$ of 81.

After a few minutes' stirring, each sample was applied to "Fabriano 2 smooth" backing paper with a laboratory doctor blade; at the end of the application the specimens were dried at room temperature for one hour.

Figure 5:
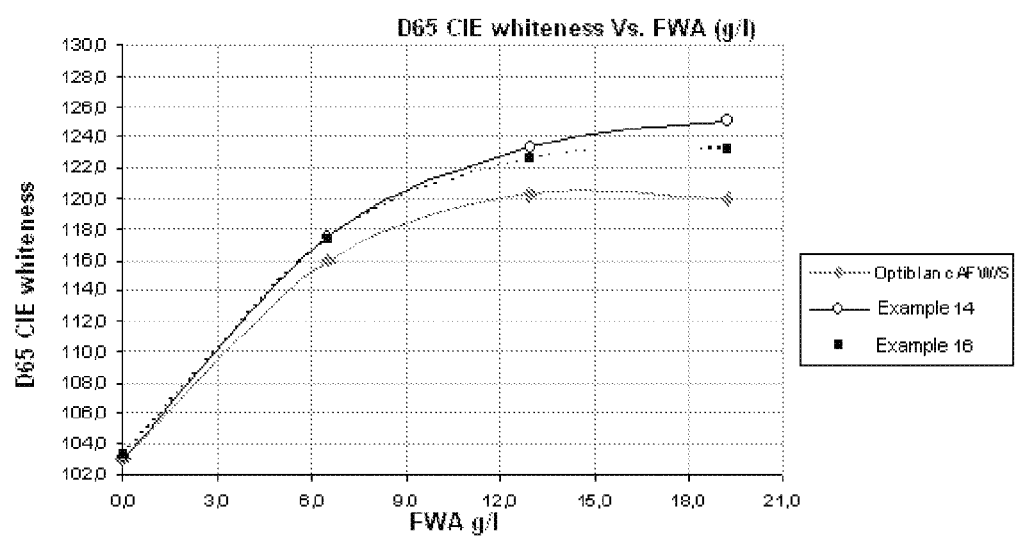
FIG. 5 shows the D65/10° CIE Whiteness values.

The degree of whiteness observed on the laboratory samples is reported in table 8 below, while the annexed FIG. 5 graphically illustrates the D65/10° CIE Whiteness values:

TABLE 8

| FWA sample | Dose (g/l) | D65 brightness | D65 CIE whiteness | L* | a* | b* |
|---|---|---|---|---|---|---|
| Optiblanc AFW/S | 0.00 | 96.2 | 103.07 | 97.43 | 1.64 | -2.16 |
| | 6.53 | 100.9 | 115.96 | 97.73 | 2.33 | -4.93 |
| | 12.95 | 103.1 | 120.24 | 98.12 | 2.00 | -5.70 |
| | 19.25 | 103.6 | 119.99 | 98.18 | 1.49 | -5.61 |
| Example 14 | 0.00 | 96.2 | 103.07 | 97.43 | 1.64 | -2.16 |
| | 6.53 | 101.0 | 117.53 | 97.73 | 2.44 | -5.29 |
| | 12.95 | 103.6 | 123.32 | 97.93 | 2.65 | -6.51 |
| | 19.25 | 104.4 | 125.07 | 97.97 | 2.66 | -6.89 |
| Example 16 | 0.00 | 96.2 | 103.27 | 97.36 | 1.61 | -2.24 |
| | 6.53 | 101.3 | 117.35 | 97.72 | 2.21 | -5.24 |
| | 12.95 | 103.5 | 122.59 | 98.07 | 2.20 | -6.27 |
| | 19.25 | 104.2 | 123.24 | 98.15 | 1.97 | -6.37 |

Example 32

Coating Application Test, Examples 20 and 21

A paper coating composition having the recipe described in example 24 was divided into 3 parts; one was left unchanged, without optical brightener, while 1.20% by weight respectively of the optical brighteners of examples 20 and 21 was added to the others.

After 5 minutes' stirring, each sample was applied to "Fabriano 2 smooth" backing paper with a Sheen 1133N automatic applicator equipped with a 1140/32/10 wire bar.

At the end of the application the specimens were dried at room temperature for 1 hour.

Table 9 below shows the optical properties detected on the samples by an ELREPHO LWE450-X reflectometer:

TABLE 9

| sample | % dose of optical brightener | D65 brightness (R457+) | D65 CIE whiteness |
|---|---|---|---|
| coating only | 0.00 | 87.6 | 78.13 |
| Example 20 | 1.20 | 94.1 | 96.75 |
| Example 21 | 1.20 | 94.6 | 98.11 |

The application yield of the various brightening agents is quantifiable by the increase in whiteness of the paper after application of the composition; both the optical brighteners demonstrated a very high level of efficiency.

Example 33

Application Test in Mixture with Example 21

186.60 grams of a mixture of bleached short-fibre eucalyptus cellulose with 38° SR (Schopper-Riegler) refinement and 3.00% dry residue was divided into in two equal parts, each containing 2.80 grams of dry cellulose.

One part was left unchanged as reference without optical brightener, while 14.00 ml of a solution of the sample of example 21 with a concentration of 2.00 g/l in demineralised water (amounting to 1.00% of optical brightener in the dry paste) was added to the second.

The samples thus obtained were used to prepare laboratory sheets with a Rapid-Koethen sheet former and dryer, and the whiteness was tested with an ELREPHO LWE450-X Datacolor reflectometer.

The values obtained are set out in table 10 below:

TABLE 10

| sample | Dose of optical brightener (%) | D65/10° brightness | D65/10° CIE whiteness | L* | a* | b* |
|---|---|---|---|---|---|---|
| Mixture only | 0.00% | 85.2 | 73.09 | 95.90 | -0.03 | 3.70 |
| Example 21 | 1.00% | 95.0 | 104.78 | 96.47 | 1.85 | -3.05 |

The application yield of the whitening agent is quantifiable as the increase in whiteness of the cellulose; the optical brightener of example 21 also demonstrated very high efficiency in this application.

Example 34

Detergent Application

Evaluation at 20° C. of the Compounds of Examples 18 and 19 in a Detergent

The samples of examples 18 and 19 were formulated at the concentration of 0.09% (specific extinction 501.6 and 514.25 respectively) in a liquid laundry detergent (heavy-duty liquid, table 11).

TABLE 11

| composition of heavy-duty liquid | |
|---|---|
| Ingredient | Percentage by weight (%) |
| Alkylbenzene sulphonate sodium salt (LAS) | 30% |
| $C_13$-$C_15$ fatty alcohol ethoxylate, 7 moles (Lutensol AO7) | 25% |
| Propylene glycol | 15% |
| Alcohol | 6% |
| Fatty acids from coconut | 14% |
| Stilbene disulphonate optical brightener example 1B | 0.52% |
| Water | to 100% |
| Monoethanolamine | to pH = 8 |

The detergent formulation was evaluated for whitening power by conducting repeated washes at 20° C. on two different types of standard fabric:

1) Empa 211 cotton fabric, whitened chemically and without optical brightener;

2) Empa 213 polyester/cotton fabric in the ratio of 65/35, whitened chemically and without optical brightener.

Experimentally, the fabrics were repeatedly washed with the same formulation, assessing the degree of whitening power by reading the surface of the fabric on the colorimeter. The colorimeter reading was performed before washing and after 1 and 3 consecutive washes. Whitening power was expressed on the Berger scale.

As reference, the same fabrics were washed with the detergent described in table 11 to which the stilbene brightener was not added, the formula being made up to 100% with water.

The experimental conditions are set out below.

TABLE 12

| | |
|---|---|
| Washing machine | Linitest |
| Hardness of water | ±20° (French) |
| Washing cycle | 10 minutes |
| Number of washes (cycles) | 3 |
| Detergent concentration | 5 g/L |
| Fabric/washing water weight ratio | 10:1 |
| Fabrics tested | Empa 211 cotton fabric, whitened chemically and without optical brightener Empa 213 polyester/cotton fabric at the ratio of 65/35, whitened chemically and without optical brightener. |
| Washing temperature | 20° C. |
| Drying conditions | 1 minute at 90° C in a Benz Dryer |
| Measuring instrument | Zeiss Elrepho 2000 colorimeter |
| Expression of whiteness | Berger scale |

The whiteness results are shown in table 13.

Both the optical brighteners of examples 18 and 19 have a much greater whitening power than the detergent "as is".

TABLE 13

| Fabric | Formulation | Before washing (Berger degrees) | 1st wash (Berger degrees) | 3rd wash (Berger degrees) |
|---|---|---|---|---|
| EMPA 211 | Optical brightener. example 18 | 81.10 | 92.26 | 101.92 |
| | Optical brightener. example 19 | 81.10 | 93.81 | 104.53 |
| | Without optical brightener | 81.10 | 83.75 | 86.85 |
| EMPA 213 | Optical brightener. example 18 | 79.20 | 86.75 | 95.07 |
| | Optical brightener. example 19 | 79.20 | 88.00 | 95.77 |
| | Without optical brightener | 79.20 | 79.85 | 81.20 |

Example 35

Cleaning Application

Evaluation at 40° C. of the Compound of Example 18 in a Detergent

The sample of Example 18 was formulated at the concentration of 0.09% (specific extinction 501.6) in a liquid laundry detergent (heavy-duty liquid, table 4).

The detergent formulation was evaluated for whitening power by conducting repeated washes at 40° C. on two different types of standard fabric:

1) Empa 211 cotton fabric, whitened chemically and without optical brightener;

2) Empa 213 polyester/cotton fabric in the ratio of 65/35, whitened chemically and without optical brightener.

Experimentally, the fabrics were repeatedly washed with the same formulation, assessing the degree of whitening power by reading the surface of the fabric on the colorimeter. The colorimeter reading was performed before washing and after 1 and 3 consecutive washes. Whitening power was expressed on the Berger scale.

As reference, the same fabrics were washed with the detergent described in table 11 of example 34 to which the optical brightener was not added, the formula being made up to 100% with water.

The experimental conditions are set out below

TABLE 14

| | |
|---|---|
| Washing machine | Linitest |
| Hardness of water | ±20° (French) |
| Washing cycle | 10 minutes |
| Number of washes (cycles) | 3 |
| Detergent concentration | 5 g/L |
| Fabric/washing water weight ratio | 10:1 |
| Fabrics tested | Empa 211 cotton fabric, whitened chemically and without optical brightener; Empa 213 polyester/cotton fabric at the ratio of 65/35, whitened chemically and without optical brightener. |
| Washing temperature | 40° C. |
| Drying conditions | 1 minute at 90° C. in a Benz Dryer |
| Measuring instrument | Zeiss Elrepho 2000 colorimeter |
| Expression of whiteness | Berger scale |

The whiteness results are shown in table 15.

The optical brightener of example 18 has a much greater whitening power than the detergent "as is".

TABLE 15

| Fabric | Formulation | Before washing (Berger degrees) | 1st wash (Berger degrees) | 3rd wash (Berger degrees) |
|---|---|---|---|---|
| EMPA 211 | Optical brightener. example 18 | 82.10 | 95.28 | 104.77 |
| | Without optical brightener | 82.10 | 84.20 | 87.04 |
| EMPA 213 | Optical brightener. example 18 | 79.20 | 88.59 | 96.12 |
| | Without optical brightener | 79.20 | 81.30 | 83.15 |

The invention claimed is:
1. Compounds of formula (I)

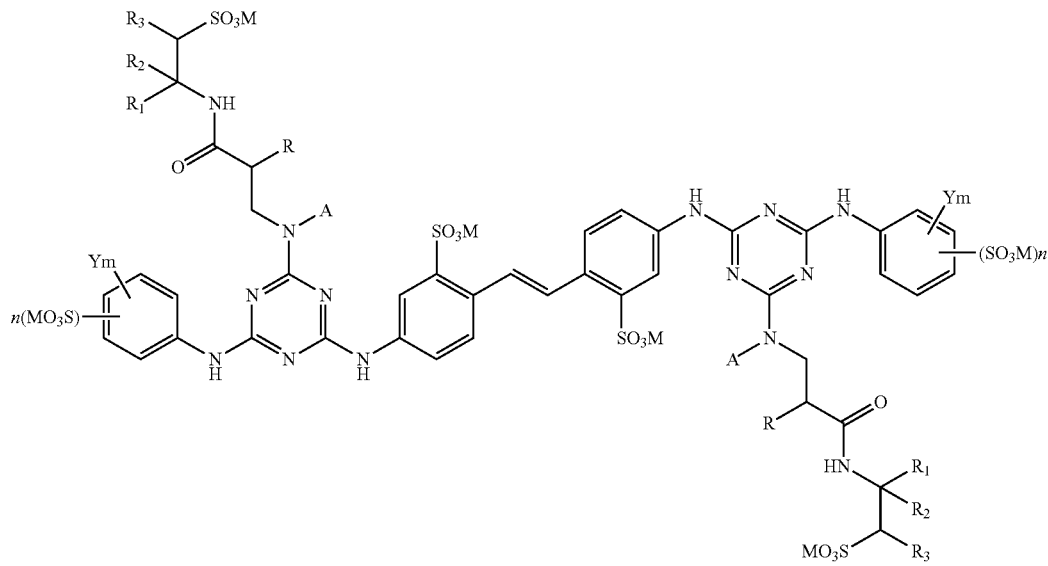

Formula (I)

wherein n is 0, 1 or 2;

Y is H, C1-C4 alkyl, LOOM, —CO—CH3, —SO2-NH2, —CN;

m is 0, 1 or 2;

R, R1, R2, R3, which can be the same or different, are H, methyl, ethyl;

the M groups are independently H, Li, Na, K, Ca, Mg, ammonium, protonated ions deriving from alkylamines, alkanolamines or alkylalkanolamines;

A is selected from the group consisting of H, C1-C8 alkyl, C3-C8 cycloalkyl, C1-C8 hydroxyalkyl, alkoxyalkyl, phenyl, alkylphenyl, the side chain of an amino carboxylic or sulphonic acid in which the carboxylic or sulphonic groups are salified with the M group as defined above, or the SO3M group, M being as defined above;

the hydrated forms thereof, either solid or in powder.

2. Compounds according to claim 1 wherein A is hydrogen, methyl, ethyl, propyl, butyl, 2-hydroxyethyl, 3-hydroxypropyl, 2-hydroxypropyl, 2-hydroxybutyl, 4-hydroxybutyl, 1,1-dimethyl-2-hydroxyethyl, phenyl.

3. Compounds according to claim 1 wherein A is a group of formula —CH2COOM, —CH(CH3)COOM, —CH(CH2OH)COOM, —CH(COOM)CH2CH(CH3)2, —CH(COOM)(CH2)4NH2, —CH(COOM)CH2COOM, —CH(COOM)(CH2)2COOM (glutamic acid), or the radicals 2-(COOM)phenyl and 4-(COOM)phenyl, in which M is as defined above.

4. Compounds according to claim 1 wherein A is the residue of a salt of an amino sulphonic acid of formula —SO3M, —CH2CH2SO3M, 3-(SO3M)-phenyl (metanilic acid), 4-(SO3M)-phenyl (sulfanilic acid), 2,4-di(SO3M)-phenyl (2,4-aniline-disulphonic acid), 2,5-di(SO3M)-phenyl (2,5-aniline-disulphonic acid) or a residue of formula (II):

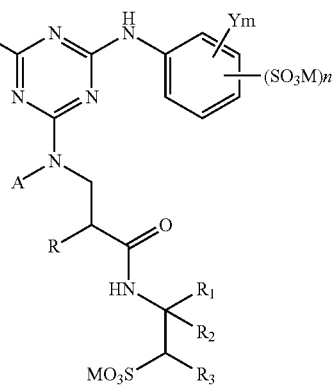

Formula (II)

wherein M, R, R1, R2 and R3 are as defined above.

5. Compounds of formula (III):

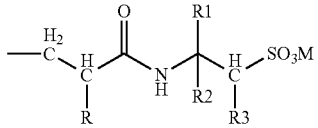

Formula (III)

wherein R, R1, R2, R3 have the meanings defined above and A is the side chain of an amino carboxylic or sulphonic acid in which the carboxylic or sulphonic groups are salified with the group M as defined in claim 1, or the group SO3M.

6. A process for the production of the compounds of formula (I) which comprises the reaction of cyanuryl chloride in three steps in the presence of water or solvents and of proton acceptors with 4,4'-diaminostylbene-2,2'-disulphonic acid, with two mols of an amine and with two mols of a different amine of formula (III).

7. A process for the production of the compounds of formula (III) which comprises the Michael addition reaction according to the following scheme:

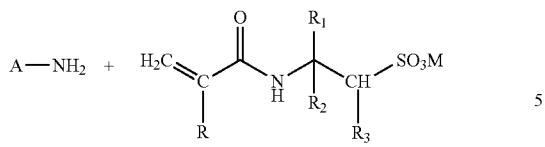

wherein A, R, R1, R2, R3 and M are as defined in claim 1.

8. Aqueous compositions for the superficial treatment of paper, comprising at least one compound of formula (I) as defined in claim 1.

9. Compositions according to claim 8 comprising at least one synthetic or natural ligand, optionally a mineral pigment and optionally other excipients selected from antifoams, dyes, dispersants, fixers, divalent metal salts, crosslinking agents, sequestering and chelating agents, lubricants, pH adjusters, biocides and preservatives, rheology and water retention modifiers.

10. Compositions according to claim 9 comprising alkali or alkaline-earth metal salts, particularly calcium chloride or magnesium chloride.

* * * * *